(12) United States Patent
Sullivan et al.

(10) Patent No.: US 10,935,436 B2
(45) Date of Patent: Mar. 2, 2021

(54) MAPPING TEMPERATURES ACROSS A SURFACE

(71) Applicant: Microsoft Technology Licensing, LLC, Redmond, WA (US)

(72) Inventors: Benjamin Sullivan, Seattle, WA (US); Siyuan Ma, Redmond, WA (US); James David Holbery, Bellevue, WA (US); Collin Alexander Ladd, Sammamish, WA (US); Kelly Marie Bogan, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 689 days.

(21) Appl. No.: 15/647,080

(22) Filed: Jul. 11, 2017

(65) Prior Publication Data

US 2019/0017879 A1 Jan. 17, 2019

(51) Int. Cl.
| | | |
|---|---|---|
| *G01K 3/00* | (2006.01) | |
| *G01K 7/04* | (2006.01) | |
| *G01K 3/14* | (2006.01) | |
| *A41D 1/00* | (2018.01) | |
| *A61B 5/01* | (2006.01) | |

(Continued)

(52) U.S. Cl.
CPC ............... *G01K 7/04* (2013.01); *A41D 1/002* (2013.01); *A61B 5/015* (2013.01); *A61B 5/6804* (2013.01); *A63B 71/00* (2013.01); *G01K 1/14* (2013.01); *G01K 3/14* (2013.01); *A41D 2500/30* (2013.01); *A63B 2230/50* (2013.01); *G01K 2213/00* (2013.01)

(58) Field of Classification Search
CPC combination set(s) only.
See application file for complete search history.

(56) References Cited

U.S. PATENT DOCUMENTS

| | | | |
|---|---|---|---|
| 3,219,993 | A | 11/1965 | Schwertz |
| 5,909,004 | A | 6/1999 | Hedengren et al. |

(Continued)

FOREIGN PATENT DOCUMENTS

| | | |
|---|---|---|
| CN | 106595886 A | 4/2017 |
| GB | 2507316 A | 4/2014 |

(Continued)

OTHER PUBLICATIONS

Dias, Tilak, "Electronic Textiles: Smart Fabrics and Wearable Technology", In Publication of Woodhead Publishing, Apr. 28, 2015, 2 pages.

(Continued)

*Primary Examiner* — Lisa M Caputo
*Assistant Examiner* — Nasir U. Ahmed
(74) *Attorney, Agent, or Firm* — Alleman Hall Creasman & Tuttle LLP

(57) ABSTRACT

Examples are disclosed that relate to mapping a plurality of temperatures across an area. One example provides a temperature sensing device including a flexible support and a temperature sensing structure having a plurality of individually readable temperature sensing junctions. The temperature sensing structure includes a line of a first conductive material extending across an area of the support, and a plurality of lines of a second conductive material each intersecting the line of the first junction material at a corresponding sensing junction.

14 Claims, 5 Drawing Sheets

(51) Int. Cl.
*A61B 5/00* (2006.01)
*A63B 71/00* (2006.01)
*G01K 1/14* (2021.01)

(56) References Cited

U.S. PATENT DOCUMENTS

| | | | | |
|---|---|---|---|---|
| 6,080,690 | A * | 6/2000 | Lebby | A41D 31/00 139/420 R |
| 6,852,395 | B2 * | 2/2005 | Dhawan | B01D 39/083 428/196 |
| 7,064,299 | B2 * | 6/2006 | Green | H05B 3/347 219/515 |
| 7,348,285 | B2 * | 3/2008 | Dhawan | D02G 3/38 174/107 |
| 8,187,984 | B2 * | 5/2012 | Rock | D06M 15/263 442/64 |
| 8,948,839 | B1 * | 2/2015 | Longinotti-Buitoni | A61B 5/6804 29/825 |
| 2007/0045593 | A1 * | 3/2007 | Yasuda | H01B 1/22 252/500 |
| 2008/0081963 | A1 | 4/2008 | Naghavi et al. | |
| 2013/0338472 | A1 * | 12/2013 | Macia Barber | A61B 5/04085 600/388 |
| 2014/0318699 | A1 * | 10/2014 | Longinotti-Buitoni | A61B 5/6805 156/247 |
| 2016/0328043 | A1 | 11/2016 | Moller et al. | |
| 2017/0049397 | A1 | 2/2017 | Sun et al. | |

FOREIGN PATENT DOCUMENTS

| | | |
|---|---|---|
| GB | 2539187 A | 12/2016 |
| WO | 2013172584 A1 | 11/2013 |

OTHER PUBLICATIONS

Locher, et al., "Temperature Profile Estimation with Smart Textiles", In Proceedings of the International Conference on Intelligent textiles, Smart clothing, Well-being, and Design, Tampere, Finland, Sep. 2005, pp. 1-8.

Koncar, Vladan, "Smart Textiles and Their Applications", In Publication of Woodhead Publishing, May 9, 2016, 1 pages.

Husain, et al., "Development of Knitted Temperature Sensor (KTS)", In Journal of SysTex, Sep. 25, 2009, 4 pages.

Ducharme, et al., "A multicouple probe for temperature gradient measurements in biological materials", In Journal of Applied Physiology, vol. 65, No. 5, Nov. 1, 1988, 1 pages.

"International Search Report and Written Opinion Issued in PCT Application No. PCT/US2018/034532", dated Sep. 4, 2018, 11 Pages.

* cited by examiner

MAPPING TEMPERATURES ACROSS A SURFACE

BACKGROUND

A thermocouple produces a temperature-dependent voltage across a junction of dissimilar conductive materials due to the Seebeck effect. Thermocouples may be used for a wide range of temperature-sensing applications, including but not limited to health, scientific, and industrial uses.

SUMMARY

Examples are disclosed that relate to mapping a plurality of temperatures across an area. One example provides a temperature sensing device comprising a flexible support and a temperature sensing structure having a plurality of individually readable temperature sensing junctions. The temperature sensing structure includes a line of a first conductive material extending across an area of the support, and a plurality of lines of a second conductive material each intersecting the line of the first junction material at a corresponding sensing junction.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Thermocouples may be used to measure temperatures in a variety of contexts. For example, thermocouple wires may be incorporated as sensors into thermometers, ovens/furnaces, water heaters, vehicles, and various probes. Such sensors often take the form of a single thermocouple junction configured to sense temperature at a single location. However, temperatures may vary over a surface area. As such, when measuring surface temperatures, a temperature reading at a single location may not provide sufficient information regarding the temperature profile over a broader area. Likewise, positioning multiple thermocouple probes across an area for sensing temperatures across the area may be inconvenient.

To sense temperatures across an area more conveniently, a plurality of thermocouple junctions may be formed on a support, such as by weaving dissimilar conductive materials into the support to form a plurality of thermocouple junctions. However, such an assembly would form plural junctions in parallel along vertical and horizontal directions. While such an assembly may be useful to measure average temperature across an area, the assembly may not be useful for sensing temperature at each individual junction across the area.

Accordingly, examples are disclosed that relate to a temperature sensing device including a flexible support comprising a temperature sensing structure that includes a plurality of individually readable temperature sensing junctions. The disclosed examples may be formed from flexible and/or stretchable materials, and may be used to map temperatures on surfaces of a range of shapes and surface topographies.

Figure 1:
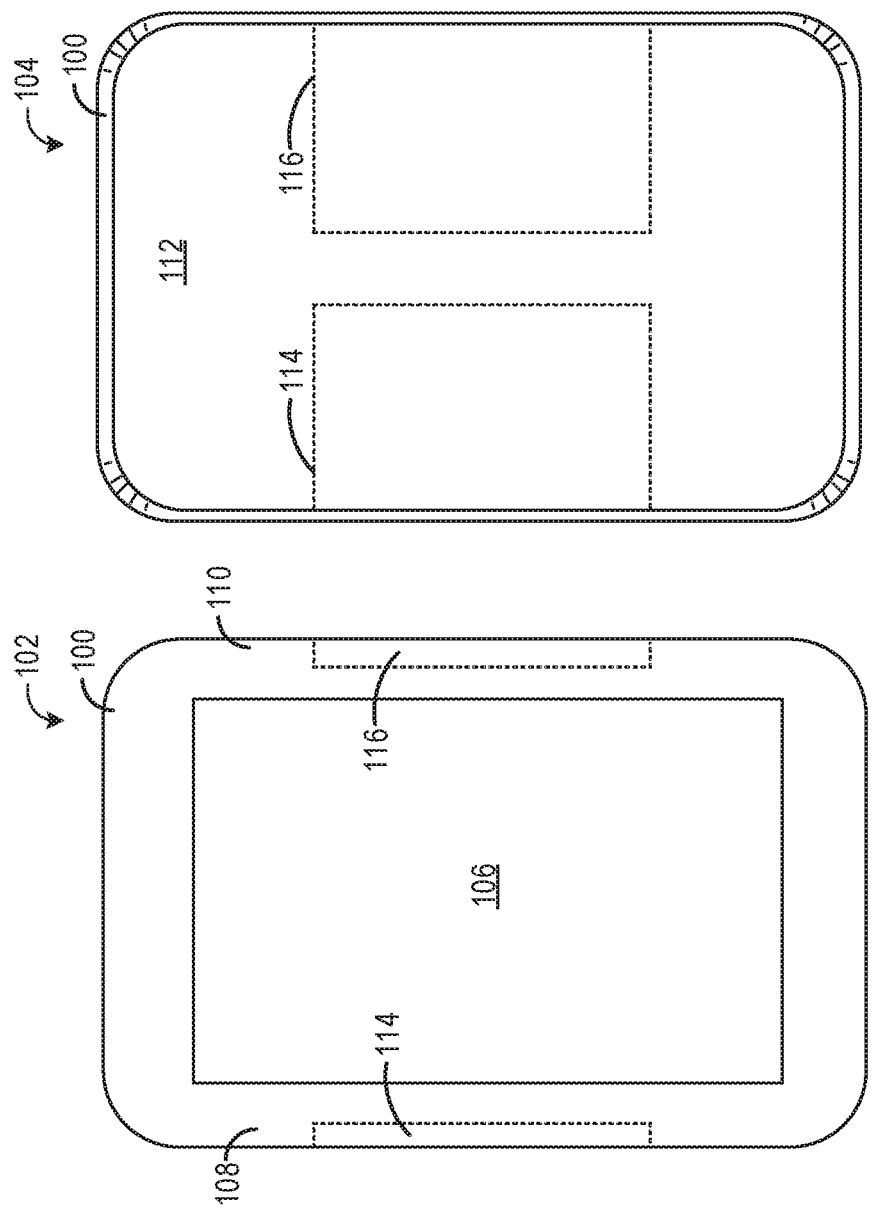
FIGS. 1A-1B show an example computing system comprising a temperature sensing device.

FIGS. 1A-1B show an example portable computing device 100 in the form of a tablet that comprises a temperature sensing device. FIG. 1A is a front view 102 of the portable computing device 100 illustrating a display 106, and FIG. 1B is a back view 104. Various surfaces of the portable computing device 100 may be formed from a soft, deformable, and/or flexible material. For example, a first side surface 108 and a second side surface 110, as well as a back surface 112 of portable computing device 100 may be at least partially formed from a fabric, elastomeric, or other soft-feeling material.

Temperature sensing structures may be integrated with such exterior surface materials to sense temperatures across the exterior surface. Such temperature sensing structures may be used, for example, to detect touches and touch gestures, or to monitor a device surface temperature for controlling a device cooling system. In the example of FIG. 1A, a first temperature sensing structure 114 may be incorporated in the material of the first side surface 108, and a second temperature sensing structure 116 may be incorporated in the material of the second side surface 110. As shown in FIG. 1B, the first temperature sensing structure 114 and the second temperature sensing structure 116 each may extend across the back surface 112 of the portable computing device 100 and wrap around sides of computing device, as example placements.

First temperature sensing structure 114 and second temperature sensing structure 116 each include a plurality of individually readable temperature sensing junctions. As described in more detail below, an individually readable temperature sensing junction may be formed at an intersection between a line of a first conductive material and a line of a second conductive material, wherein the lines are arranged to form a matrix of individually readable sensing locations. Portable computing device 100 also includes a processor and storage comprising stored instructions executable by the processor to monitor the outputs of temperature sensing structures for such interactions, and to perform an action on the portable computing device responsive to a temperature-based input detected by one or more of the temperature sensing structures. Any suitable actions may be performed. Examples include, but are not limited to, actions in response to touch and/or gesture inputs made by a user over the temperature sensing structures, and actions in response to determining a device temperature is out of a predetermined temperature range. More details on an example computing system are described below with reference to FIG. 5.

Figure 2:
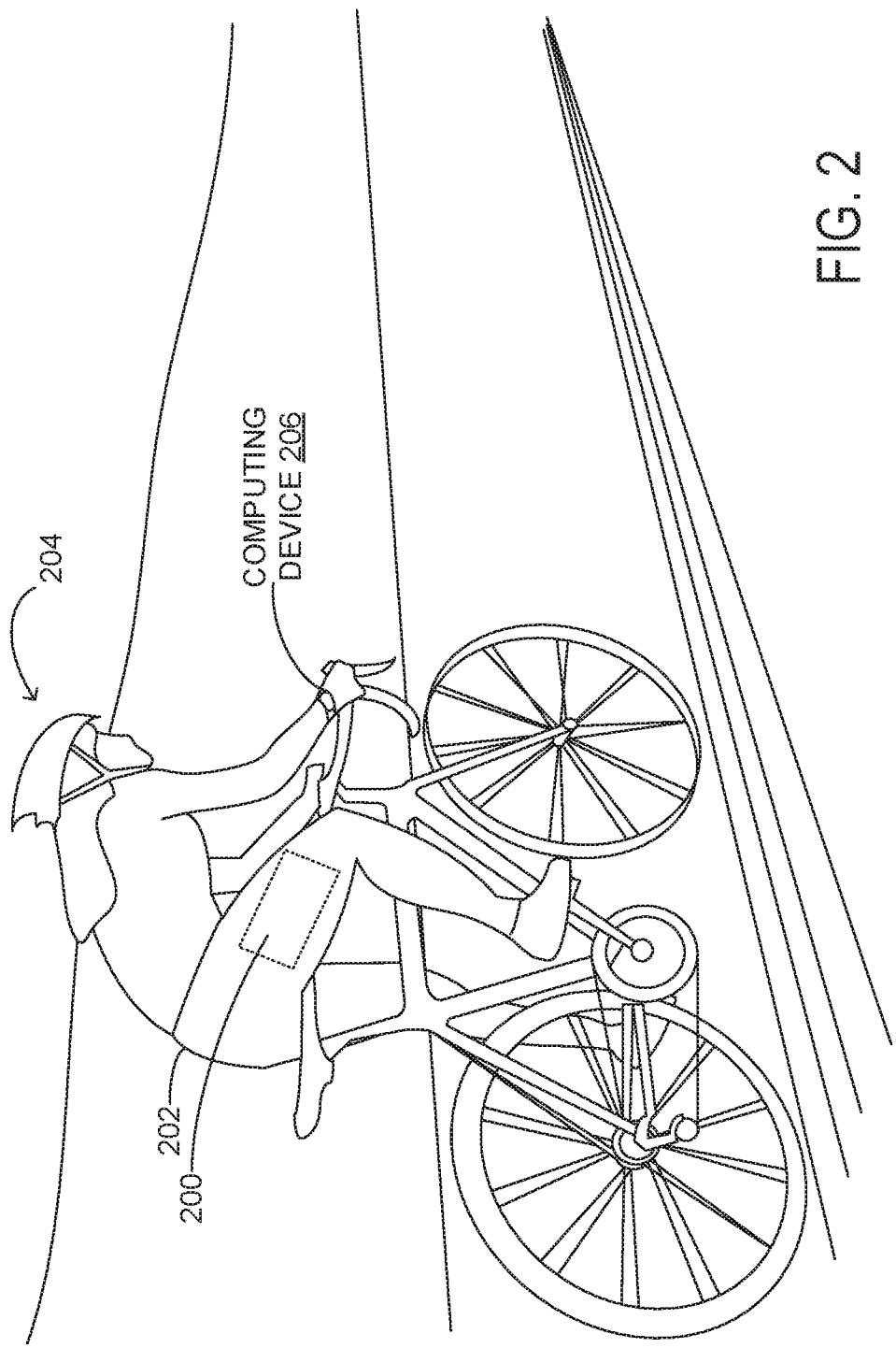
FIG. 2 shows an example temperature sensing device integrated with a clothing item.

A temperature sensing device also may be used to provide outputs to a remotely-located computing device via a wired or wireless connection, rather than being integrated with a computing system. FIG. 2 illustrates an example temperature sensing device 200 in the form of a clothing item 202 used to provide temperature data to a computing device 206 in the form of a wrist band. Temperature sensing device 200 may be configured to have a suitably close fit to one or more body part of a user 204 to sense a user's temperature profile across an area of the user's skin. Device 200 may be used, for example, to monitor changes in temperature that occur during and/or after exercise. This may allow computing device 206 to monitor a condition of user 204 for risks such as hyperthermia or hypothermia, and to notify user 204 and/or others of any such detected condition. As a more specific example, temperature sensing devices located at a body core and a body extremity may allow a user to monitor whether his or her body temperature at an extremity (e.g. hands, feet) is significantly higher or lower than a core temperature so that the user 204 can take appropriate precautions. While shown in the context of a pair of biking pants, it will be understood that a wearable temperature sensing device as disclosed herein may be used in any other suitable wearable item. Further, in some examples, a temperature sensing device as disclosed herein may be used in other flexible articles, such as furniture upholstery, bedding (e.g. for monitoring body temperatures of hospital patients), bandages, wraps, and blankets.

A temperature sensing device according to the present disclosure may have any suitable shape. For example, a temperature sensing device may be formed as a flexible flat sheet that can be draped over non-flat objects, or shaped to fit a particular non-flat surface, such as a specific device or a specific human anatomical part. A temperature sensing device as disclosed herein may utilize any suitable flexible support material. Examples include woven textiles and nonwoven textiles (including stretchable fabrics), knitted textiles, and suitable non-textile materials, such as polymer sheets (including elastomer sheets).

Figure 3:
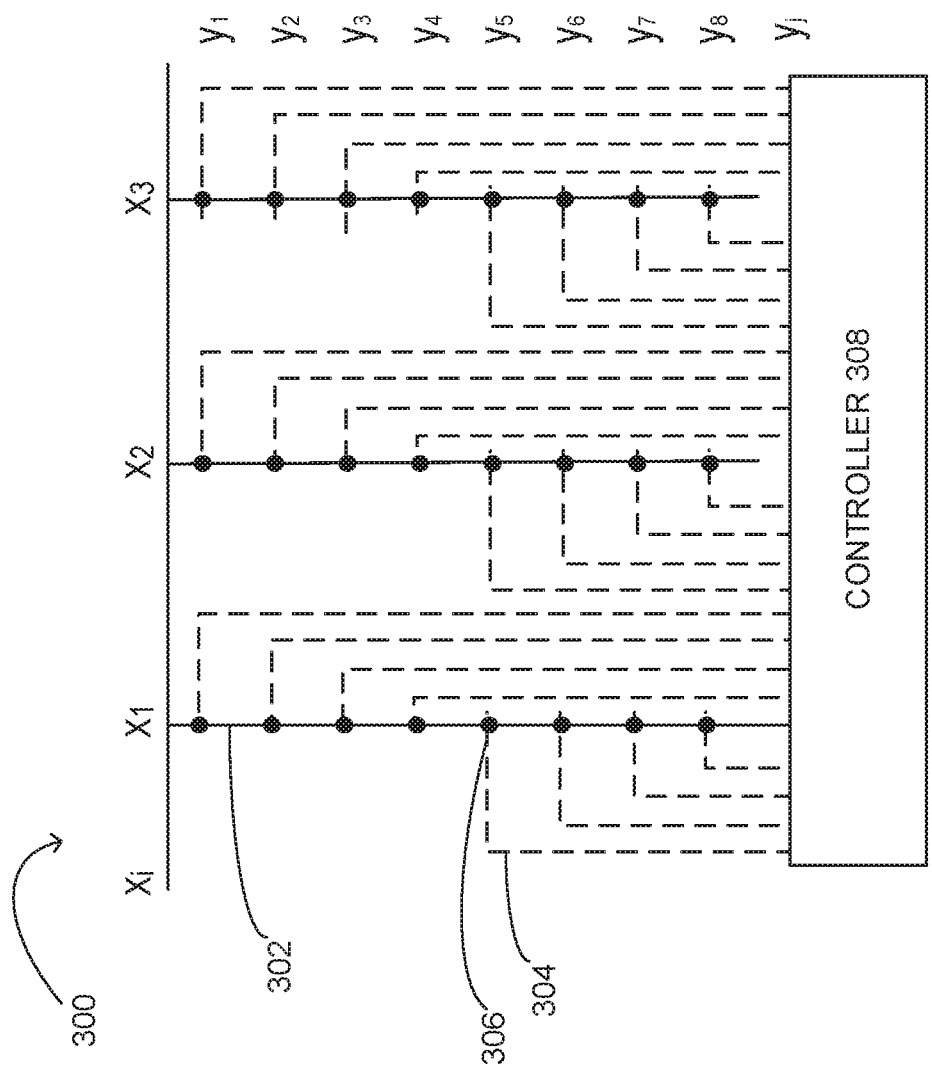
FIG. 3 shows an example configuration of a temperature sensing structure for a temperature sensing device.

FIG. 3 shows a schematic depiction of an example temperature sensing structure 300 for use in a flexible item. Temperature sensing structure 300 includes a line of a first conductive material 302 extending in a desired pattern or trace across an area of a flexible support, and a plurality of lines of a second conductive material 304 each intersecting the line of the first conductive material 302 at a corresponding temperature sensing junction 306. Each temperature sensing junction $x_i y_j$ yields a voltage that may be read and interpreted by a controller 308, which may associate a temperature with the voltage measured at each temperature sensing junction 306. In other examples, a plurality of lines of first conductive material 302 electrically connected to a common ground may be used.

As described above, temperature sensing structure 300 is integrated with a flexible support, such as a fabric of clothing item 202 shown in FIG. 2. The flexible support may comprise any suitable material. In some examples in which the flexible support comprises a woven textile, temperature sensing structure 300 may be integrated as conductive fibers woven into the textile. Conductive fibers also may be integrated into a knitted textile. In yet other examples, temperature sensing structure 300 may comprise conductive fibers embroidered or otherwise sewn into the flexible support to form temperature sensing junctions. The term fiber as used herein refers to a conductive substance with a high length-to-width ratio and is the main component used to construct a continuous strand, also referred to as yarns, threads, filaments, wires, and/or any other material suitable for weaving, sewing, embroidering, knitting, laminating or adhering on or into a flexible support. Further, in some examples, conductive materials for forming thermocouple junctions may be printed onto a flexible support.

Any suitable materials may be used for the first and second conductive materials. For example, the first conductive material and the second conductive material each may comprise an elemental metal (e.g. silver, copper, nickel), metal alloy, conductive composite material (e.g. a metal- or carbon-containing polymer), a semiconductor-containing material (e.g. tin selenide), and/or a coated material (e.g. a conductive coating formed on a non-conductive core).

In some examples, a fiber of the first conductive material and of the second conductive material may be stretchable and flexible, such as yarns comprising elastic materials. Such yarns may be formed, for example, from a conductive filament wound around an elastic core.

In some examples, one or both of the first conductive material and the second conductive material of the temperature sensing structure 300 may be printed (for example, by screen printing or ink jet printing) on the flexible support. In such examples, a line of a first conductive ink may be printed across an area of the flexible support and/or a plurality of lines of a second conductive material each may be printed to intersect the line of the first conductive ink at a corresponding temperature sensing junction. Where one but not both conductive materials are printed, the other conductive material may take the form of a fiber sewn, woven, laminated, adhered, or otherwise integrated with the flexible support. Any suitable conductive ink may be used to print conductive lines in such examples. Examples include, but are not limited to, inks comprising silver, carbon, copper, nickel, and PEDOT:PSS (polyethylenedioxythiophene:polystyrene sulfonic acid). Further in examples where the flexible support is stretchable, the ink may be configured to maintain conductivity when printed. Examples of stretchable inks include inks having an elastomer binder and anisotropically shaped conductive particles, such as metal flakes or nanowires, that maintain contact as the ink is stretched. Additionally, transparent conductors may be used in a transparent or translucent thermocouple array. Examples of such materials include, but are not limited to, ITO, ATO (antimony doped tin oxide), FTO (Fluorine doped tin oxide), doped zinc oxide, silver nanowires and PEDOT:PSS.

Figure 4:
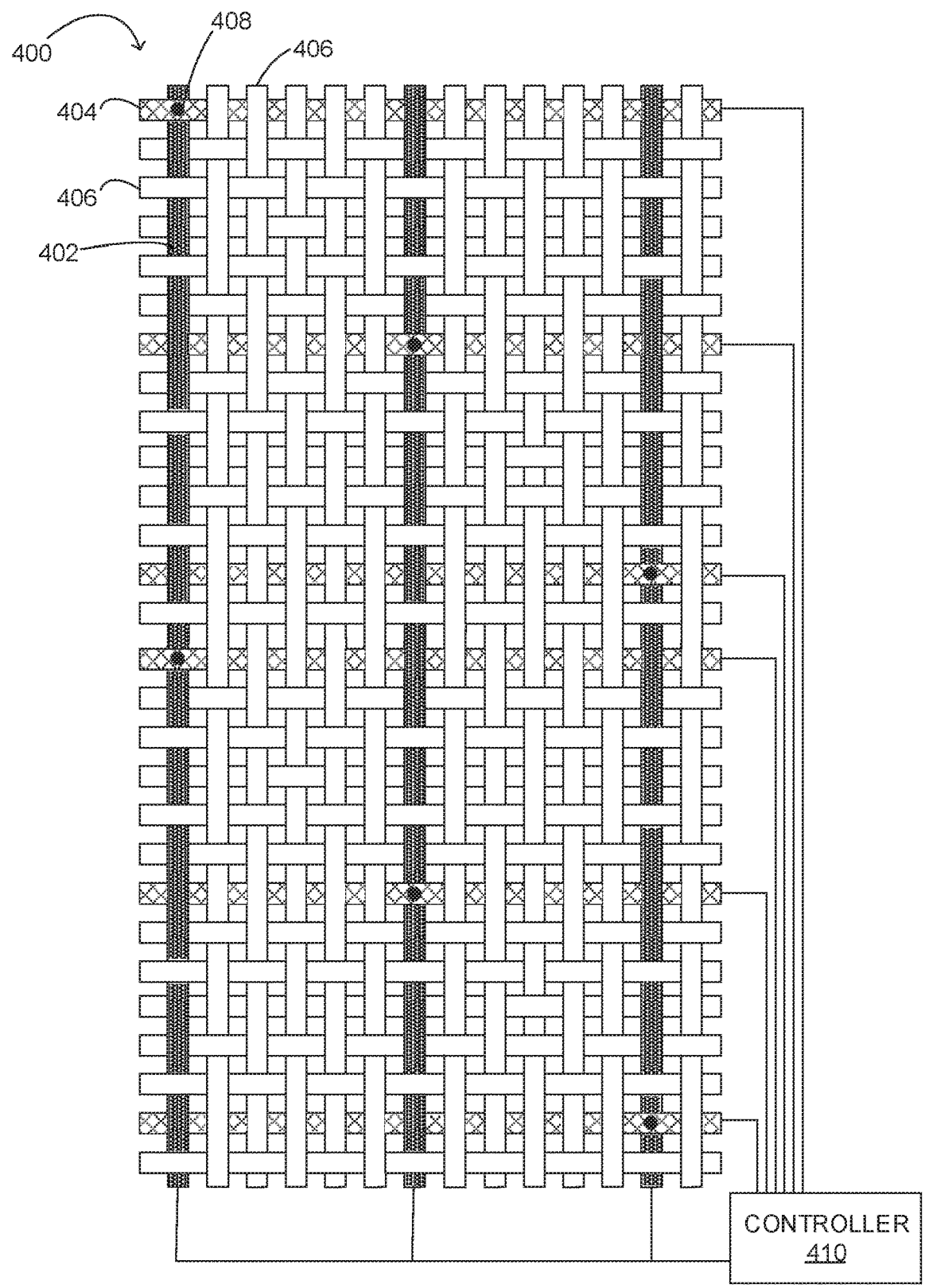
FIG. 4 schematically depicts an example temperature sensing structure in the form of a woven textile.

FIG. 4 schematically shows an example temperature sensing structure 400 in the form of a woven textile that incorporates individually readable temperature sensing junctions. Temperature sensing structure 400 comprises fibers of a first conductive material 402, a second conductive material 404, and a non-conductive material 406 woven to form individually readable temperature sensing junctions 408. In this example, conductive fibers are not interlaced at intersections of conductive materials where junctions are not desired, and are interlaced at specific intersections to contact the two conductors and thereby form junctions. Temperature sensing structure 400 is one example of a woven structure comprising thermocouple junctions, and any other suitable woven structure may be used. As another example, a leano weave may be used, in which a pair of warp yarns may be twisted around a weft yarn at locations to form a junction, and not twisted at locations where junctions are not desired. In some examples, the conductive materials at each junction may be twisted or knotted to ensure contact between the materials. Further, in some examples, a weld, solder, or adhesive joint may be used to maintain contact at each junction. In such examples, the junction may be mechanically robust, which may help to avoid noise generation at the electrode interface. Other suitable structures also may be used to create mechanically robust junctions.

The non-conductive material 406 may comprise any suitable electrically insulating material. Examples include traditional natural and synthetic fabric fibers used for weaving, such that the temperature sensing structure 400 has a touch and feel similar to traditional fabric items. Non-conductive material 406 may help to prevent fibers of the first conductive material 402 and of the second conductive material 404 from making unintended contact with one another, thereby helping to prevent shorting. In some examples, lines of the first conductive material and lines of the second conductive material may be sheathed or encapsulated such that a conductive portion of each material is exposed at junctions and electrically insulated elsewhere.

Likewise, the first conductive material 402 and the second conductive material 404 each may be formed from any suitable electrically conductive material. In some examples, the first conductive material 402 and the second conductive material 404 each may be formed from a conductive yarn that incorporates one or more fibers of an electrically conductive element, alloy, or composite. Examples of suitable materials include those mentioned elsewhere herein. Cost, accuracy, sensitivity, stability, operative range and/or other factors, may be considered when selecting materials.

Temperature sensing structure 400 further comprises a controller 410 configured to read, and in some examples interpret, voltages at each temperature sensing junction 408. In other examples, temperature data from controller 410 may be provided via a communication subsystem to another computing device.

It will be understood that the various temperature sensing devices and temperature sensing structure configurations illustrated in FIGS. 1-4 are presented for the purpose of example, and that other devices and configurations may be used without departing from the scope of the disclosure.

In some embodiments, the methods and processes described herein may be tied to a computing system of one or more computing devices. In particular, such methods and processes may be implemented as a computer-application program or service, an application-programming interface (API), a library, and/or other computer-program product.

Figure 5:
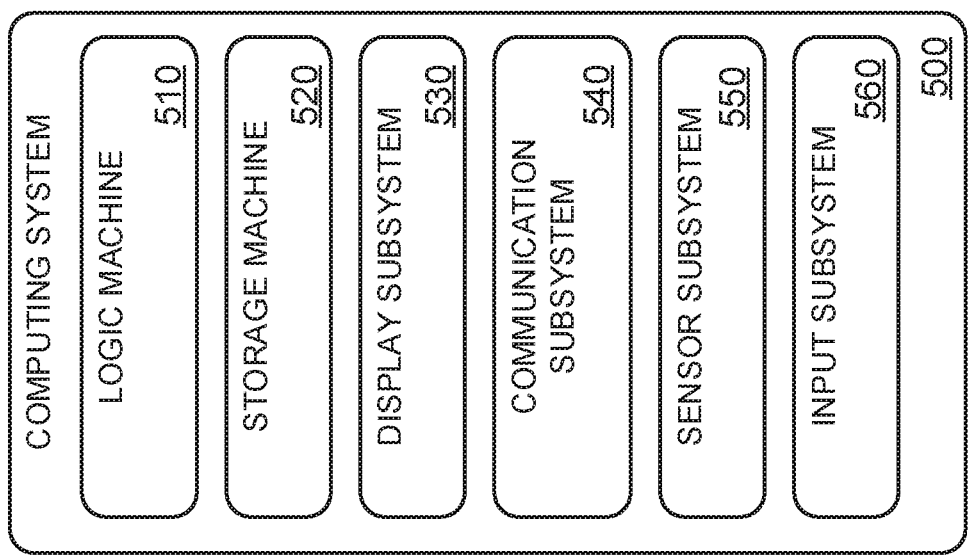
FIG. 5 shows an example computing system.

FIG. 5 schematically shows a non-limiting embodiment of a computing system 500 that can enact one or more of the methods and processes described above. Computing system 500 is shown in simplified form. Computing system 500 may take the form of one or more personal computers, server computers, tablet computers, home-entertainment computers, network computing devices, gaming devices, mobile computing devices, mobile communication devices (e.g., smart phone), and/or other computing devices. Computing system 500 is a non-limiting example of portable computing device 100, computing device 206 and controller 410 described above with respect to FIGS. 1, 2 and 4, respectfully.

Computing system 500 includes a logic machine 510 and a storage machine 520. Computing system 500 may optionally include a display subsystem 530, input subsystem 560, communication subsystem 540, sensor subsystem 550, and/or other components not shown in FIG. 5.

Logic machine 510 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 520 includes one or more physical devices configured to hold instructions executable by the logic machine to implement the methods and processes described herein. When such methods and processes are implemented, the state of storage machine 520 may be transformed—e.g., to hold different data.

Storage machine 520 may include removable and/or built-in devices. Storage machine 520 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 520 may include volatile, nonvolatile, dynamic, static, read/write, read-only, random-access, sequential-access, location-addressable, file-addressable, and/or content-addressable devices.

It will be appreciated that storage machine 520 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 510 and storage machine 520 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 530 may be used to present a visual representation of data held by storage machine 520. This visual representation may take the form of a graphical user interface (GUI). As the herein described methods and processes change the data held by the storage machine, and thus transform the state of the storage machine, the state of display subsystem 530 may likewise be transformed to visually represent changes in the underlying data. Display subsystem 530 may include one or more display devices utilizing virtually any type of technology. Such display devices may be combined with logic machine 510 and/or storage machine 520 in a shared enclosure, or such display devices may be peripheral display devices.

When included, input subsystem 560 may comprise or interface with one or more user-input devices such as a keyboard, mouse, touch screen, or game controller. In some embodiments, the input subsystem may comprise or interface with selected sensors of sensor subsystem 550, such as natural user input (NUI) componentry. Such componentry may be integrated or peripheral, and the transduction and/or processing of input actions may be handled on- or off-board. Example NUI componentry included in sensor subsystem 550 may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Sensor subsystem 550 may include one or more temperature sensing structure 114, 116, 300, 400 described above with respect to FIGS. 1, 3, and 4.

When included, communication subsystem 540 may be configured to communicatively couple computing system 500 with one or more other computing devices. Communication subsystem 540 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 500 to send and/or receive messages to and/or from other devices via a network such as the Internet.

Another example provides a temperature sensing device for mapping a plurality of temperatures across an area, the temperature sensing device comprising a flexible support, and a temperature sensing structure comprising a plurality of individually readable temperature sensing junctions, the temperature sensing structure comprising a line of a first conductive material extending across an area of the flexible support, and a plurality of lines of a second conductive material each intersecting the line of the first junction material at a corresponding sensing junction. In such an example, the temperature sensing device additionally or alternatively may comprise a plurality of temperature sensing structures integrated with the flexible support. In such an example, the flexible support additionally or alternatively may comprise a woven textile. In such an example, one or more of the line of the first conductive material and the plurality of lines of the second conductive material additionally or alternatively may comprise a conductive fiber woven into the woven textile. In such an example, the flexible support additionally or alternatively may comprise a non-woven textile. In such an example, one or more of the flexible support, the first conductive material, and the second conductive material additionally or alternatively may comprise a stretchable material. In such an example, the flexible support additionally or alternatively may comprise a polymer sheet. In such an example, the flexible support additionally or alternatively may comprise a knitted textile. In such an example, one or more of the line of the first conductive material and the plurality of lines of the second conductive material may additionally or alternatively be embroidered into the flexible support. In such an example, one or more of the line of the first conductive material and the plurality of lines of the second conductive material may additionally or alternatively be printed on the flexible support. In such an example, one or more the first conductive material and the second conductive material additionally or alternatively may comprise a metallic fiber. In such an example, the temperature sensing device additionally or alternatively may comprise a soldered, welded or adhesive joint at one or more of the sensing junctions.

Another example provides a temperature sensing device for mapping a plurality of temperatures across an area, the temperature sensing device comprising a flexible support, and a temperature sensing structure comprising a plurality of individually readable temperature sensing junctions, the temperature sensing structure comprising a line of a first conductive ink extending across an area of the flexible support, and a plurality of lines of a second conductive material each intersecting the line of the first conductive ink at a corresponding temperature sensing junction. In such an example, the first conductive ink additionally or alternatively may comprise one or more of nickel and carbon, and the second conductive ink additionally or alternatively may comprise silver. In such an example, one or more of the first conductive ink and the second conductive material additionally or alternatively may comprise an elastomer binder and anisotropically shaped conductive particles. In such an example, the flexible support additionally or alternatively may comprise a fabric support. In such an example, the flexible support may additionally or alternatively comprise a polymer support.

Another example provides a temperature sensing device for mapping a plurality of temperatures across an area, the temperature sensing device comprising a flexible textile, and a temperature sensing structure comprising a plurality of individually readable temperature sensing junctions, the temperature sensing structure comprising a fiber of a first conductive material incorporated with the flexible textile and extending through an area of the flexible textile, and a plurality of fibers of a second conductive material incorporated with the flexible textile, each fiber of the second conductive material intersecting the fiber of the first conductive material at a corresponding temperature sensing junction. In such an example, the flexible textile additionally or alternatively may comprise a woven structure. In such an example, the flexible textile additionally or alternatively may comprise a non-woven structure.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A temperature sensing device for mapping a plurality of temperatures across an area, the temperature sensing device comprising:
   a flexible textile comprising a plurality of fibers of a non-conductive material; and
   a temperature sensing structure comprising a plurality of individually readable temperature sensing junctions, the temperature sensing structure comprising a plurality of fibers of a first conductive material integrated into and extending across an area of the flexible textile, and a plurality of fibers of a second conductive material integrated into and extending across the area of the flexible textile along a different direction than the plurality of fibers of the first conductive material,
   wherein each fiber of the plurality of fibers of the second conductive material comprises a single junction with a corresponding fiber of the first conductive material to form a sensing junction.

2. The temperature sensing device of claim 1, further comprising a plurality of temperature sensing structures integrated with the flexible textile.

3. The temperature sensing device of claim 1, wherein the flexible textile comprises a woven textile.

4. The temperature sensing device of claim 3, wherein one or more of the plurality of fibers of the first conductive material and the plurality of fibers of the second conductive material comprises a conductive fiber woven into the woven textile.

5. The temperature sensing device of claim 1, wherein the flexible textile comprises a non-woven textile.

6. The temperature sensing device of claim 1, wherein one or more of the flexible textile, the first conductive material, and the second conductive material comprises a stretchable material.

7. The temperature sensing device of claim 1, wherein the flexible textile comprises a knitted textile.

8. The temperature sensing device of claim 1, wherein one or more of the plurality of fibers of the first conductive material and the plurality of fibers of the second conductive material is embroidered into the flexible textile.

9. The temperature sensing device of claim 1, wherein one or more the first conductive material and the second conductive material comprises a metallic fiber.

10. The temperature sensing device of claim 1, further comprising a soldered, welded or adhesive joint at one or more of the sensing junctions.

11. A temperature sensing device for mapping a plurality of temperatures across an area, the temperature sensing device comprising:
 a flexible textile comprising a plurality of fibers of a non-conductive material; and
 a temperature sensing structure comprising a plurality of individually readable temperature sensing junctions, the temperature sensing structure comprising
  a plurality of fibers of a first conductive material integrated into and extending through an area of the flexible textile; and
  a plurality of fibers of a second conductive material integrated into and extending through the area of the flexible textile along a different direction than the plurality of fibers of the first conductive material,
  wherein each fiber of the plurality of fibers of the second conductive material is interlaced with a corresponding fiber of the first conductive material at a single junction to contact the first conductive material and the second conductive material to form a sensing junction.

12. The temperature sensing device of claim 11, wherein the flexible textile comprises a woven structure.

13. The temperature sensing device of claim 11, wherein the flexible textile comprises a non-woven structure.

14. The temperature sensing device of claim 11, wherein one or more of the flexible textile, the first conductive material, and the second conductive material comprises a stretchable material.

* * * * *